United States Patent [19]

Gonella

[11] 4,411,909

[45] Oct. 25, 1983

[54] [(2-OXO-3-TETRAHYDROTHIENYLCAR-BAMOYL)-ALKYLTHIO] ACETIC ACIDS, THEIR SALTS AND ESTERS, A PROCESS FOR PREPARATION THEREOF AND THE PHARMACEUTICAL COMPOSITIONS CONTAINING SAME

[75] Inventor: Jacques Gonella, Zollikon, Switzerland

[73] Assignee: Refarmed, Recherches Pharmaceutiques et Medicales, S.A., Switzerland

[21] Appl. No.: 358,370

[22] Filed: Mar. 15, 1982

[30] Foreign Application Priority Data

Mar. 19, 1981 [FR] France .................................. 8105496

[51] Int. Cl.³ .................. A61K 31/38; C07D 333/16
[52] U.S. Cl. ...................... 424/275; 549/63
[58] Field of Search .................................. 549/63, 549/69; 424/275

[56] References Cited

U.S. PATENT DOCUMENTS 4,241,078 12/1980 Chan .................................. 549/63

*Primary Examiner*—Alan Siegel

*Attorney, Agent, or Firm*—Ostrolenk, Faber, Gerb & Soffen

[57] ABSTRACT

The present invention relates to [(2-oxo-3-tetrahydrothienylcarbamoyl)-alkylthio]-acetic acids, their salts and esters of formula:

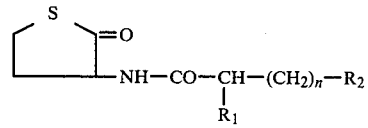

in which n is 0 or 1, one of the substituents $R_1$ and $R_2$ is a hydrogen atom or a methyl group and the other represents a group $-S-CH_2-COOR_3$, where $R_3$ is a hydrogen atom or an alkali metal or a lower alkyl group or a group:

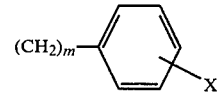

It also relates to a process for preparing said acids, salts and esters, and to the drugs containing same.

8 Claims, No Drawings

[(2-OXO-3-TETRAHYDROTHIENYLCAR-BAMOYL)-ALKYLTHIO] ACETIC ACIDS, THEIR SALTS AND ESTERS, A PROCESS FOR PREPARATION THEREOF AND THE PHARMACEUTICAL COMPOSITIONS CONTAINING SAME

The present invention relates to novel [(2-oxo-3-tetrahydrothienylcarbamoyl)-alkylthio]acetic acids having a mucolytic activity, to a process for preparation thereof and to pharmaceutical compositions containing same as active ingredients.

More particularly, according to one of its aspects, the invention relates to novel compounds having the following general formula:

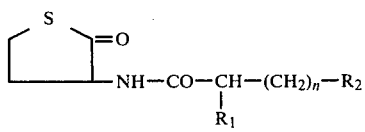

in which n represents 0 or 1 and one of the substituents $R_1$ and $R_2$ represents a hydrogen atom or a methyl group and the other represents an $S-CH_2-COOR_3$ group where $R_3$ is a hydrogen atom or an alkali metal or an $R_3'$ group, $R_3'$ being lower alkyl or a group

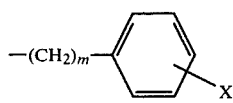

where m represents 0 or 1 and X represents a hydrogen atom, or a lower alkyl, lower alkoxy or nitro group.

The term "lower alkyl" as indicated here designates an alkyl group of from 1 to 3 carbon atoms, namely the methyl, ethyl, propyl and isopropyl groups. The terms "lower alkoxy" and "lower alkylthio" designate the hydroxyl and sulfhydryl groups where the hydrogen atom is replaced by a lower alkyl group as designated hereinabove.

According to another of its aspects, the present invention relates to a process for preparing [(2-oxo-3-tetrahydrothienylcarbamoyl)-alkylthio]acetic acids of formula I, characterised in that a 3-haloacylamino-2-oxo-tetrahydrothiophene of formula:

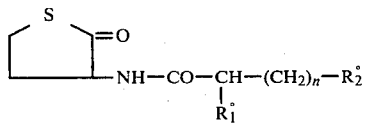

where one of the $R_1°$ and $R_2°$ is a hydrogen atom or a methyl group and the other a chlorine or bromine atom, is reacted with a thioglycolic acid of formula:

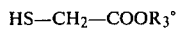

$$HS-CH_2-COOR_3°$$    III where $R_3°$ has the meaning given hereinabove for $R_3$, but is other than an alkali metal, in the presence of a proton acceptor at a temperature of 15° to 120° C. and, when $R_3°$ is hydrogen, the product thus obtained is possibly converted into its alkali salts.

An inorganic base such as sodium or potassium hydroxide, sodium or potassium carbonate, sodium or potassium bicarbonate, or an organic base such as trimethylamine, triethylamine or piperidine may be used as proton acceptor.

Water or an organic solvent may be used as reaction diluent. Operation is preferably carried out in water in the presence of sodium or potassium hydroxide.

The reaction is rapid and its duration (from 2 to 30 mins.) depends on the temperature. Generally, after 5 mins. of heating to reflux in an aqueous solution, the reaction is complete and the final product is isolated according to conventional techniques, for example by addification and filtration or by acidification and extraction with an appropriate solvent.

If, as intermediate product of formula III, the free thioglycolic acid ($R_3°=H$) is used, a free acid of formula $1(R_3=H)$ is obtained which may be salified according to conventional techniques to obtain an alkali salt ($R_3=$alkali metal.

According to a variant of the process of the present invention, the free acid of formula I ($R_3=H$) may be esterified with a compound of formula $R_3'-OH$, where $R_3'$ is such as defined hereinabove, according to conventional techniques.

Esterification is conducted by reacting a functional derivative of said free acid, such as chloride or a mixed anhydride, with compound $R_3'-OH$ at a temperature of $-20°$ to $+40°$ C. in the presence of a proton acceptor in an inert organic solvent.

According to a preferred modus operandi, the free acid is treated with ethyl chlorocarbonate and with compound $R_3'-OH$ in the presence of an organic base, preferably triethylamine, at a temperature of $-15°$ to $-10°$ C.

A hydrocarbon, particularly hexane, benzene or toluene, is preferably used as organic solvent, but other solvents inert in the conditions of esterification, such as dioxane, are also suitable.

The resultant ester is isolated in conventional manner, by elimination of the impurities, evaporation of the solvent and crystallization.

The [(2-oxo-3-tetrahydrothienylcarbamoyl)-alkylthio]acetic acids of the present invention possess advantageous pharmacological properties without any toxicity.

In particular, the compounds of the present invention are capable of provoking an increase in the production of bronchial mucus in animals, as has been demonstrated in a test of activity in the rabbit.

Rabbits were used weighing about 3 kg with a cannula implanted in the trachea according to the technique of Scuri et al., Boll. Chim. Farm., 119,(3), 1980. The quantity of mucus produced and excreted was recorded during the 4 hours preceding and the 4 hours following the treatment.

Table I hereinbelow shows the results obtained with a compound representative of the present invention, [(2(oxo-3-tetrahydrothienylcarbamoyl)-methylthio]acetic acid, hereinafter indicated by its code No. PV 144. A well known product with mucolytic action, S-carboxymethylcysteine, hereinafter indicated by its common international name "carbocysteine", was used as reference product. The products were administered by the intravenous route and the results are expressed in percentage of the variation of secretion of mucus with respect to the controls having received physiological solution.

TABLE I

| Product | dose | variation % |
| --- | --- | --- |
| PV 144 | 10 mg/kg (0.04 mmol/kg) | 52.1 |
| carbocysteine | 10 mg/kg (0.055 mmol/kg) | 51.8 |

This Table shows that the product of the present invention is at least as active as the reference product at the same dose by weight which corresponds to a molar dose of PV 144 lower by 37.5% than that of the reference compound.

In the test of mucolytic activity based on the inhalation of $SO_2$ in the rat, the compounds of the present invention have shown a good mucolytic activity. In particular, the PV 144 at the oral dose of 500 mg/kg (2 mmol/kg) included a significant regression of the damage provoked by the action of sulfur dioxide on the bronci. This regression is qualitatively and quantitatively equal to that obtained by a dose of 500 mg/kg (3.35 mmol/kg) of carbocysteine.

Table II below shows the data of acute toxicity determined in the rat and the mouse by the oral and intravenous routes on a compound representative of the present invention, PV 144.

TABLE II

| | PV 144 $LD_{50}$ (mg/kg) | |
| --- | --- | --- |
| Animal | oral | i.v. |
| Mouse | >10000 | >3500 |
| Rat | >10000 | >3500 |

The Table shows that the product representative of the present invention is virtually without toxicity.

Due to their mucolytic activity, the [(2-oxo-3-tetrahydrothienylcarbamoyl)-alkylthio]acetic acids of the present invention may be used in the treatment of diseases in the respiratory apparatus; in particular, they may be used in pneumology in bronchites, in tracheobronchites, in pharyngites, in rhinopharyngites, in otites, and in sinusites.

The products of the present invention may be administered by the oral, parenteral or rectal route or by inhalation either alone or in the form of appropriate pharmaceutical preparations such as tablets, powders, granules, capsules, elixirs, suspensions, syrups, suppositories and solutions or suspensions for injection or for inhalation.

The pharmaceutical preparations intended for oral administration contain, in addition to the active substance, one or more pharmaceutically acceptable organic or mineral excipients compatible with the active ingredient, as well as sweetening agents, flavouring agents, colorants, conservation agents and the like.

For preparing tablets, the excipients may be constituted by inert diluents such as calcium carbonate, sodium carbonate, lactose, talc, granulation and disaggregation agents such as starch and alginic acid, binding agents such as starch, gelatine and gum arabic, lubricating agents such as magnesium stearate and stearic acid. The tablets may or may not be coated.

The purpose of such coating is to delay decomposition and absorption of the active substance in the gastrointestinal tract and thus to produce an prolonged delay effect. The suspensions, syrups and elixirs may contain, in addition to the active substance, suspension agents such as methylcellulose, gum tragacanth, sodium alginate and the like, wetting agents such as lecithin, polyoxyethylene stearate, polyoxyethylenesorbitan monooleate and conservation agents such as ethyl p-hydroxybenzoate. The capsules may contain the active substance either alone or mixed with solid inert diluents such as for example calcium carbonate, calcium phosphate and kaolin.

Fluids for oral administration are prepared in dosage unit form, such as syrups where each coffee spoonful of composition contains a predetermined quantity of the active compound to be administered.

A syrup is prepared by suspending the active ingredient in an aqueous solution of saccharose appropriate flavoured for example by vanillin or oil of lemons.

Granules intended for reconstitution of a liquid preparation for oral administration are prepared by using water-soluble diluents. The active compound and a water-soluble diluent such as saccharose, glucose, etc. are wetted with a binding agent such as gum arabic, solution of gelatine, solution of methylcellulose and the product is strained through a sleve by force to form granules which are dried. It is advantageous to introduce into the composition a suspension agent such as gum tragacanth.

The granules thus obtained may be packed in sachets and thus administered in dosage unit form.

For parenteral administration, the compositions according to the invention may be in the form of ampoules containing the active principle dissolved in a solvent for injection, water for injection or preferably a physiological solution. The dosage unit may also be in the form of a sterile ampoule for preparing extemporaneous solutions for parenteral administration.

For administration by inhalation, the compositions according to the invention may be in the form of a powder or an aerosol spray; the same ampoules as for parenteral administration may also be used.

The compositions of the present invention may also contain other active products such as for example antibiotics, bronchodilatators, antitussives, balsamics, antihistaminics or local anaesthetics.

The compositions of the present invention contain from 1 to 1000 mg of active ingredient per dosage unit and may be administered so as to furnish a dose of active substance varying from 4 to 2000 mg per day.

The following examples illustrate the invention without limiting the scope thereof.

EXAMPLE 1

To a solution of 76.5 g of sodium hydroxide in 470 ml of water are added, in a nitrogen atmosphere, 30.5 g of thioglycolic acid and then 64 g of 3-chloroacetamido-2-oxo-tetrahydrothiophene. The mixture is heated to reflux for 5 mins. then cooled, acidified with hydrochloric acid concentrated up to pH 1 to 2 and filtered.

By crystallization with 500 ml of ethanol, 40 g of [(2-oxo-3-tetrahydrothienylcarbamoyl)-methylthio]acetic acid are obtained (PV 144), m.p. 156° to 158° C.

To a solution of 24.9 g of the product thus obtained in 50 ml of water are added 5.3 g of sodium carbonate and the limpid solution thus obtained is evaporated to dryness and the residue is crystallized with 150 ml of 85% ethanol. 28 g of [(2-oxo-3-tetrahydrothienylcarbamoyl)-methylthio]acetate of sodium are obtained.

Similarly, from 24.9 g of [(2-oxo-2-tetrahydrothienylcarbamoyl)-methylthio]acetic acid and from 6.9 g of potassium carbonate, 28 g of [(2-oxo-3-tetrahydrothienylcarbamoyl)-methylthio]acetate of potassium are obtained.

EXAMPLE 2

To a solution of 32 g of sodium hydroxide in 800 ml of water are added, in a nitrogen atmosphere, 37 g of thioglycolic acid then 101 g of 3-(2-bromoprobromopropionamido)-2-oxo-tetrahydrothiophene, then the product is heated for 5 minutes at reflux, cooled and acidified with hydrochloric acid concentrated up to clearly acid pH (1 to 2). It is extracted with 400 ml of chloroform, the organic phase is dried over anhydrous sodium sulfate and evaporated to dryness under reduced pressure. The oily residue, constituted by [1-(2-oxo-3-tetrahydrothienylcarbanioyl)-ethylthio]acetic acid, is dissolved in 100 ml of acetone and there is added to the acetonic solution the calculated quantity of potassium carbonate dissolved in a very small quantity of water. The precipitate thus obtained is filtered and crystallized in 500 ml of ethanol. In this way, 105 g of [1-(2-oxo-3-tetrahydrothienylcarbamoyl)ethylthio]acetate of potassium are obtained; m.p. 202° to 204° C.

By replacing the potassium carbonate by an equivalent quantity of sodium carbonate, the corresponding sodium salt is obtained.

EXAMPLE 3

To a solution of 4 g of sodium hydroxide in 20 ml of water are added, in a nitrogen atmosphere, 12 g of thioglycolate of ethyl and then 25.2 g of 3-(2-bromopropionamido)-2-oxo-tetrahydrothiophene. The mixture is heated for 5 minutes at reflux, then cooled, extracted twice with 20 l of chloroform, the organic phase is dried over anhydrous sodium sulfate and the solvent is evaporated to dryness under reduced pressure. By crystallization of the residue in diethyl ether/ethanol, 24 g of [1-(2-oxo-3-tetrahydrothienylcarbomoyl)ethylthio]acetate of ethyl are obtained; m.p. 80° to 85° C.

In the same way, from 3-bromoacetamido-2-oxo-tetrahydrothiophene, [(2-oxo-3-tetrahydrothienylcarbamoyl)methylthio]acetate of ethyl is obtained.

EXAMPLE 4

To a solution of 9.8 g of ethyl thioglycolate and 16.9 g of 3-(3-chloropropiomamido)-2-oxo-tetrahydrothiophene in 200 ml of dimethylsulfoxide are added 5.4 g of 85% potassium hydroxide dissolved in a minimal quantity of water. After 30 mins. at ambient temperature, 500 ml of water are added and the mixture is extracted with 200 ml of chloroform. The organic phase is dried over anhydrous sodium sulfate and the solvent is evaporated under reduced pressure. By crystallization of the residue in isopropanol, 14 g of [2-(2-oxo-3-tetrahydrothienylcarbamoyl)ethylthio]acetate of ethyl are obtained; m.p. 59° to 60° C.

In the same way, from 5.34 g of 3-(2-bromobutyramido)-2-oxo-tetrahydrophiophene and 2.4 g of ethylthioglycolate, 4.7 g of [1-(2-oxo-3-tetrahydrothienylcarbamoyl)propylthio]acetate of ethyl are obtained, after crystallization in diethyl ether; m.p. 45° to 47° C.

EXAMPLE 5

A solution of 22 g of triethylamine in 50 ml of anhydrous toluene is slowly added to a suspension, cooled to −10° C., of [(2-oxo-3-tetrahydrothienylcarbamoyl)-methylthio]acetic acid and 22 g of ethyl chlorocarbonate in 500 ml of anhydrous toluene. A solution of 19 g of phenol in 200 ml of anhydrous toluene is then added at the same temperature, then the reaction mixture is left for 30 minutes at ambient temperature, is filtered and extracted firstly with a saturated solution of sodium bicarbonate then with water. The organic phase is dried over anhydrous sodium sulfate and the solvent is evaporated under reduced pressure. By crystallization of the residue in ethanol, 51 g of [(2-oxo-3-tetrahydrothienylcarbamoyl)-methylthio]acetate of phenyl are obtained; m.p. 99° to 101° C.

In the same way, by reacting 50 g of [(2-oxo-3-tetrahydrothienylcarbamoyl)-methylthio]acetic acid, 22 g of triethylamine and 22 g of ethyl chlorocarbonate, in 500 ml of a anhydrous toluene with, respectively, 25 g of guaiacol and 30.8 g of p-nitrobenzyl alcohol, the following are respectively obtained: 52.5 g of [(2-oxo-3-tetrahydrothienylcarbamoyl)methylthio]acetate of 2-methoxyphenyl which, after crystallization in ethanol, melts at 105°–106° C. and 57 g of [(2-oxo-3-tetrahydrothienylcarbamoyl)methylthio]acetate of p-nitrobenzyl which, after crystallization in ethanol, melts at 99°–100° C.

EXAMPLE 6

A syrup having the following composition is prepared:

| | |
|---|---|
| PV 144 sodium salt | 2 g |
| saccharose | 70 g |
| methyl p-hydroxybenzoate | 0.15 g |
| flavouring agent | 1.25 g |
| water   q.s.p. | 100 ml |

EXAMPLE 7

A syrup having the following composition is prepared:

| | |
|---|---|
| PV 144 sodium salt | 5 g |
| saccharose | 40 g |
| methyl p-hydroxybenzoate | 0.15 g |
| flavouring agent | 2 g |
| water   q.s.p. | 100 ml |

EXAMPLE 8

Tablets containing 300 mg of PV 144 are prepared in the following way: 60 kg of PV 144, 12 kg of lactose and 8 g of corn starch are granulated with 4 kg of polyvinylpyrrolidone (molecular weight about 25,000) in 6 liters of water and are passed through a sieve with a mesh diameter of 1.25 mm.

After drying, 10 kg of carboxymethylcellulose, 4 kg of talc and 2 kg of magnesium stearate are added. The granulate is compressed into tablets on a drum pelletizer, said tablets having a diameter of 11 mm and weighing 500 mg. Similarly, tablets containing 150 and 500 mg of PV 144 are prepared.

EXAMPLE 9

10,000 capsules containing 50 mg of active substance are prepared from the following constituents: 500 g of PV 144, 495 g of microcrystalline cellulose, 5 g of amorphous silica gel are mixed well and introduced into capsules of hard gelatine of dimension 4.

Capsules containing 100 and 200 mg of PV 144 are prepared in the same way.

What is claimed is:

1. [(2-oxo-3-tetrahydrothienylcarbamoyl)-alkylthio]-acetic acid, salt or ester, fof formula:

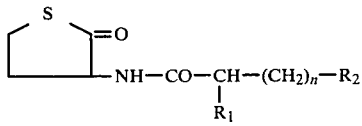

in which n represents 0 or 1 and one of the substituents $R_1$ and $R_2$ represents a hydrogen atom or a methyl group and the other represents a $-S-CH_2-COOR_3$ group, where $R_3$ is a hydrogen atom or an alkali metal or a group $R_3'$, $R_3'$ being a lower alkyl or a group:

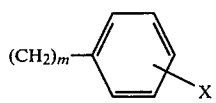

where m represents 0 or 1 and X represents a hydrogen atom, or a lower alkyl, lower alkoxy or nitro group.

2. [(2-oxo-3-tetrahydrothienylcarbamoyl)-methylthio]-acetic acid of formula:

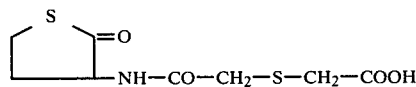

and the sodium and potassium salts thereof.

3. [(2-oxo-3-tetrahydrothienylcarbamoyl)-methylthio]-acetate of ethyl.

4. [(2-oxo-3-tetrahydrothienylcarbamoyl)-methylthio]-acetate of phenyl.

5. [(2-oxo-3-tetrahydrothienylcarbamoyl)-methylthio]-acetate of 2-methoxyphenyl.

6. Process for preparing [(2-oxo-3-tetrahydrothienylcarbamoyl)-alkylthio]-acetic acid of formula:

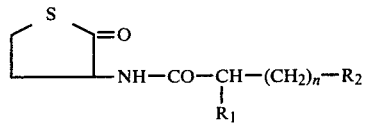

in which n represents 0 or 1 and one of the substituents $R_1$ and $R_2$ represents a hydrogen atom or a methyl group and the other represents a group $-S-CH_2-COOR_3$, where $R_3$ is a hydrogen atom or an alkali metal or a group

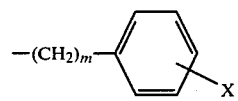

where m represents 0 or 1 and X represents a hydrogen atom, or a lower alkyl, lower alkoxy or nitro group, comprising reacting a 3-halocylamino-2-oxo-tetrahydrothiophene of formula

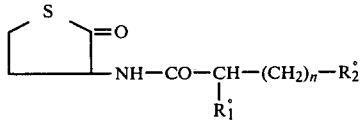

in which one of the substituents $R_1°$ and $R_2°$ represents a hydrogen atom or a methyl group and the other represents a chlorine or bromine atom, with a thioglycolic acid of formula:

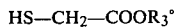

HS—CH$_2$—COOR$_3°$ in which $R_3°$ has the meaning defined hereinabove for $R_3$, but is other than an alkali metal, in the presence of a proton acceptor at a temperature of 15° to 120° C., when $R_3°$ is hydrogen.

7. Pharmaceutical composition containing, as active ingredient, a compound according to claim 1 mixed with a pharmaceutical excipient.

8. The pharmaceutical composition of claim 6, in dosage unit form, containing from 1 to 1000 mg of the compound according to claim 1 mixed with a pharmaceutical excipient.

9. The pharmaceutical composition of claims 6 or 7, wherein it contains, as active ingredient, [(2-oxo-3-tetrahydrothienylcarbamoyl)-methylthio]-acetic acid or its sodium or potassium salt.

* * * * *